United States Patent
Vellagoundar et al.

(10) Patent No.: US 10,878,311 B2
(45) Date of Patent: Dec. 29, 2020

(54) IMAGE QUALITY-GUIDED MAGNETIC RESONANCE IMAGING CONFIGURATION

(71) Applicant: General Electric Company, Schenectady, NY (US)

(72) Inventors: Jaganathan Vellagoundar, Bangalore (IN); Ashok Kumar P. Kumar Reddy, Bangalore (IN); Manivannan Jayapalan, Bangalore (IN)

(73) Assignee: General Electric Company, Schenectady, NY (US)

( * ) Notice: Subject to any disclaimer, the term of this patent is extended or adjusted under 35 U.S.C. 154(b) by 187 days.

(21) Appl. No.: 16/146,770

(22) Filed: Sep. 28, 2018

(65) Prior Publication Data

US 2020/0104674 A1 Apr. 2, 2020

(51) Int. Cl.
| | | |
|---|---|---|
| G06N 3/04 | (2006.01) | |
| G06N 3/08 | (2006.01) | |
| G16H 30/20 | (2018.01) | |
| G16H 40/20 | (2018.01) | |
| G16H 30/40 | (2018.01) | |
| G06T 7/00 | (2017.01) | |

(52) U.S. Cl.
CPC .......... G06N 3/0454 (2013.01); G06N 3/08 (2013.01); G06T 7/0012 (2013.01); G16H 30/20 (2018.01); G16H 30/40 (2018.01); G16H 40/20 (2018.01)

(58) Field of Classification Search
CPC ........ G06N 3/0454; G06N 3/08; G06N 3/084; G06N 3/02; G06N 3/0445; G06N 3/0472; G06N 3/0481; G16H 40/20; G16H 40/63; G16H 30/20–40; G16H 50/20; G06T 7/0012; G06T 7/11; G06T 2207/20081–20084; G06T 2207/10081; G06T 2207/10132; G06T 2207/30004; G06T 5/002; A61B 6/032; A61B 6/545; A61B 6/037; A61B 6/488; A61B 6/503; A61B 6/5217; A61B 5/055; A61B 5/0035; A61B 8/5223; G06F 19/321
See application file for complete search history.

(56) References Cited

U.S. PATENT DOCUMENTS

| | | | |
|---|---|---|---|
| 4,835,690 A | 5/1989 | Gangarosa et al. | |
| 6,687,527 B1 | 2/2004 | Wu et al. | |
| 6,781,375 B2 | 8/2004 | Miyazaki et al. | |
| 10,043,088 B2 * | 8/2018 | Odry | G06K 9/627 |
| 10,198,799 B2 * | 2/2019 | Park | G06T 5/001 |
| 10,241,175 B2 * | 3/2019 | Benner | G01R 33/56527 |
| 10,387,765 B2 * | 8/2019 | Mailhe | G06N 3/084 |

(Continued)

FOREIGN PATENT DOCUMENTS

WO 2017116011 7/2017

*Primary Examiner* — Michael S Osinski

(57) ABSTRACT

Apparatus, systems, and methods for improved imaging device configuration are disclosed and described. An example apparatus includes a memory storing a first neural network that is trained to map image quality metrics to corresponding scan parameters. The example apparatus includes a processor configured to: receive specified image quality metrics; instruct the trained first neural network to generate scan parameters based on the specified image quality metrics to configure an imaging device for image acquisition; and instruct the imaging device to acquire one or more resulting images using the generated scan parameters.

17 Claims, 10 Drawing Sheets

(56) References Cited

U.S. PATENT DOCUMENTS

| | | |
|---|---|---|
| 10,572,998 B2 * | 2/2020 | Bhatia .................... A61B 6/032 |
| 2006/0255801 A1 | 11/2006 | Ikeda |
| 2007/0276221 A1 | 11/2007 | Warntjes |
| 2012/0190962 A1 * | 7/2012 | Glaser-Seidnitzer ........................ G16H 40/63 600/407 |
| 2015/0199478 A1 * | 7/2015 | Bhatia .................... A61B 6/503 382/128 |
| 2017/0143312 A1 * | 5/2017 | Hedlund ............... G06N 3/0445 |
| 2017/0154054 A1 * | 6/2017 | Gao ......................... G06F 16/51 |
| 2018/0071452 A1 * | 3/2018 | Sharma .................. G16H 40/60 |
| 2018/0144466 A1 | 5/2018 | Hsieh et al. |
| 2018/0160981 A1 * | 6/2018 | Tsymbalenko ........ A61B 8/5215 |
| 2018/0349759 A1 * | 12/2018 | Isogawa .................. G06N 3/084 |
| 2019/0057504 A1 * | 2/2019 | Kobayashi ............. G06T 7/0014 |
| 2019/0164312 A1 * | 5/2019 | Sunkavalli ................ G06N 3/08 |
| 2019/0282205 A1 * | 9/2019 | Tung .................... A61B 8/5253 |
| 2019/0282214 A1 * | 9/2019 | Park ......................... G06T 7/11 |
| 2019/0294930 A1 * | 9/2019 | Koike .................... G01N 21/64 |
| 2019/0340754 A1 * | 11/2019 | Honkala ................ A61B 6/5211 |
| 2019/0355114 A1 * | 11/2019 | Muehlberg ................ G06T 7/11 |
| 2019/0365341 A1 * | 12/2019 | Chan .................... G06T 7/0012 |
| 2019/0374165 A1 * | 12/2019 | Poole .................... G16H 30/40 |
| 2020/0005100 A1 * | 1/2020 | Kim ...................... G06K 9/6217 |
| 2020/0043602 A1 * | 2/2020 | Kim ........................ G16H 50/20 |
| 2020/0069214 A1 * | 3/2020 | Takeshima ............. A61B 5/055 |
| 2020/0069292 A1 * | 3/2020 | Abolmaesumi ........ A61B 8/463 |
| 2020/0075164 A1 * | 3/2020 | Lieberman ............. G16H 50/20 |
| 2020/0075165 A1 * | 3/2020 | Lieberman ............. G06F 40/30 |
| 2020/0082943 A1 * | 3/2020 | Sakaguchi ............. G06N 20/00 |
| 2020/0088824 A1 * | 3/2020 | Takeshima ......... G01R 33/5673 |
| 2020/0098106 A1 * | 3/2020 | Moriyasu .............. G06T 7/0012 |

* cited by examiner

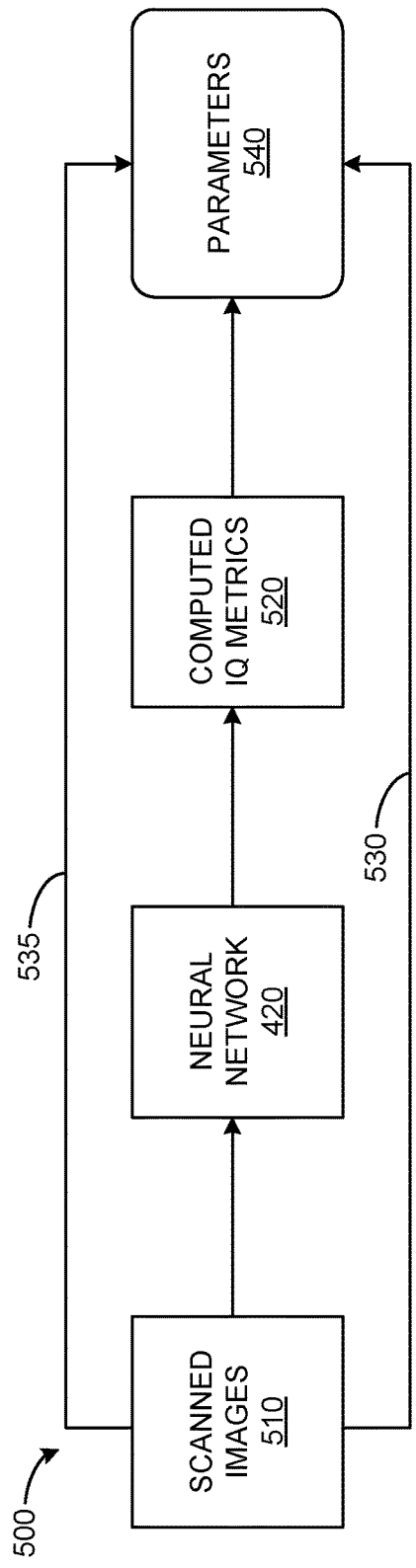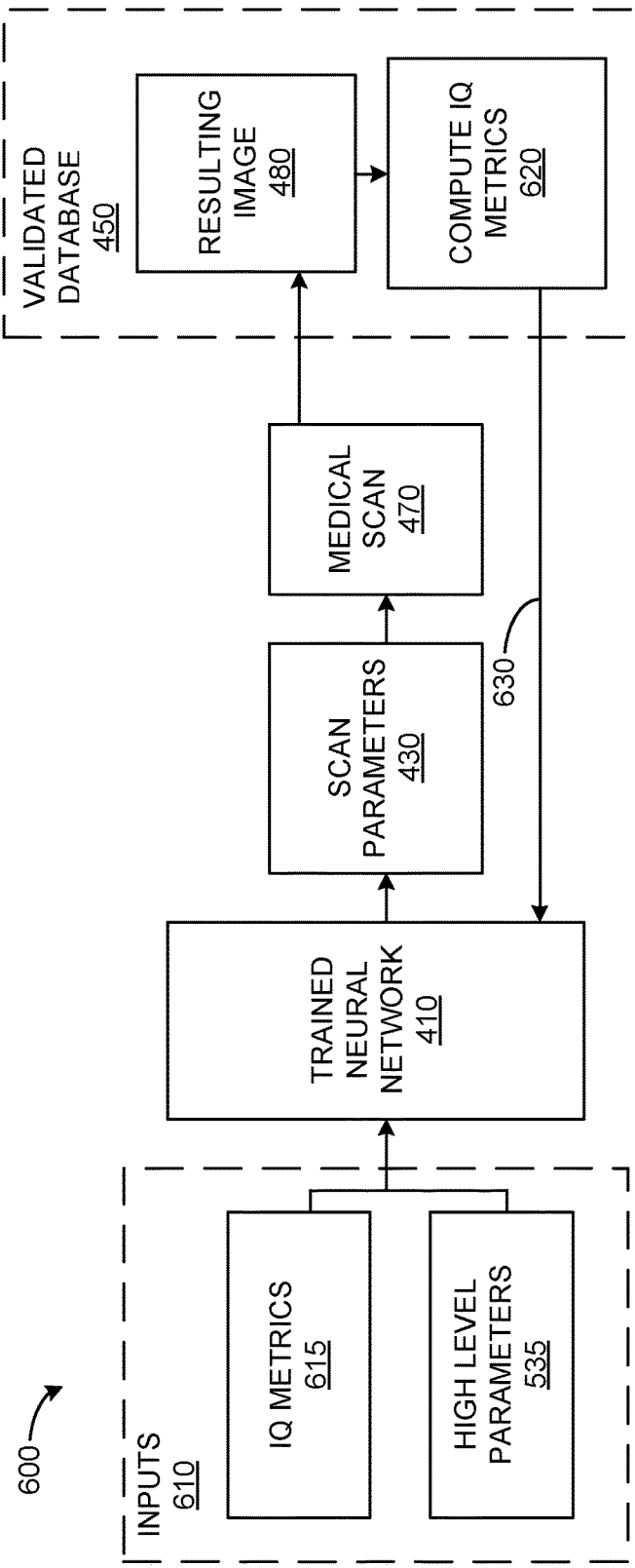

IMAGE QUALITY-GUIDED MAGNETIC RESONANCE IMAGING CONFIGURATION

FIELD OF THE DISCLOSURE

This disclosure relates generally to improved imaging systems and, more particularly, to improved image quality-guided magnetic resonance imaging configuration.

BACKGROUND

Current methods of magnetic resonance (MR) imaging involve usage of multiple sequences based on a body part to be imaged as well as clinical aspects of the body part and/or, more generally, the patient under study. Imaging capabilities are effectuated through selection of a large number of quantitative input scan parameters including scan resolution, inter-echo spacing, bandwidth, etc. Different MR scanning systems can have anywhere from twenty to forty input parameters. The different input parameters work together and can restrict the dynamic range of other parameters as well as the final image quality. A technician must consider the many parameters, as well as time constraints, when performing a MR scan. Many technicians performing MR scans lack the high level of knowledge required to understand the various interactions between the parameters. In addition to the lack of proper knowledge, a technician that is often pressed for time may select parameters that are not optimal to the functioning of the MR system. As a result, image quality can be greatly degraded, which, in turn limits the value of any clinical results.

BRIEF DESCRIPTION

Certain examples provide systems and methods for improved imaging device configuration.

Certain examples provide an apparatus including a memory storing a first neural network that is trained to map image quality metrics to corresponding scan parameters. The example apparatus includes a processor configured to: receive specified image quality metrics; instruct the trained first neural network to generate scan parameters based on the specified image quality metrics to configure an imaging device for image acquisition; and instruct the imaging device to acquire one or more resulting images using the generated scan parameters.

Certain examples provide a non-transitory computer-readable storage medium storing: a first neural network that is trained to map image quality metrics to corresponding scan parameters; and instructions. The instructions, when executed, cause at least one processor to at least: receive specified image quality metrics; instruct the trained first neural network to generate scan parameters based on the specified image quality metrics to configure an imaging device for image acquisition; and instruct the imaging device to acquire one or more resulting images using the generated scan parameters.

Certain examples provide a computer-implemented method including: training a first neural network, using image quality metrics and scan parameters associated with image datasets, wherein the image quality metrics are output from a second neural network that maps the image datasets to corresponding image quality metrics; receiving, by at least one processor, specified image quality metrics; generating, by the trained first neural network, corresponding scan parameters based on the specified image quality metrics to configure an imaging device for image acquisition; and instructing, by the at least one processor, the imaging device to acquire one or more resulting images using the generated scan parameters.

BRIEF DESCRIPTION OF THE DRAWINGS

FIG. 5 illustrates an example network training environment to generate parameters to train a network.

FIG. 6 illustrates an example testing and validation phase to confirm that the updated network is ready to be deployed to configure imaging systems for image acquisition.

The figures are not scale. Wherever possible, the same reference numbers will be used throughout the drawings and accompanying written description to refer to the same or like parts.

DETAILED DESCRIPTION

Figure 1:
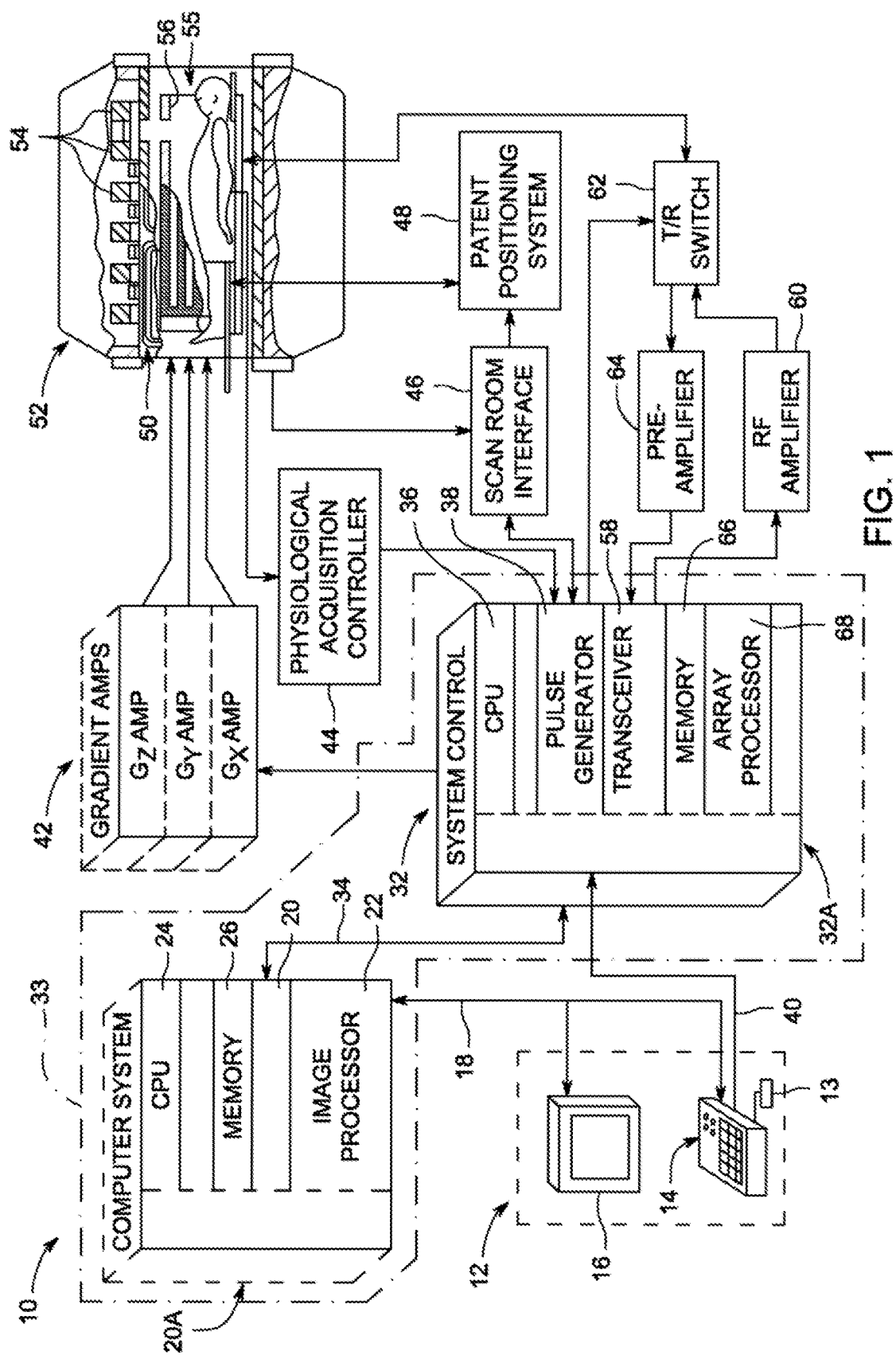
FIGS. 1-2 illustrate an example imaging system to which the methods, apparatus, and articles of manufacture disclosed herein can be applied.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. OVERVIEW

Imaging devices (e.g., gamma camera, positron emission tomography (PET) scanner, computed tomography (CT)

scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

In certain examples, deep learning and/or other machine learning networks can be configured to determine an image acquisition prescription or otherwise form a data structure to instantiate parameters/settings for image acquisition based on a desired image quality (IQ). In certain examples, multiple deep learning networks are used to generate an image acquisition prescription. For example, a first network (e.g., a regression network, etc.) computes image acquisition prescription parameters based on the desired IQ and scan time chosen (e.g., chosen by a user, specified by a program, imaging protocol, and/or other system, etc.) to form an image acquisition "prescription" or configuration data structure. A regression network is lighter weight and less computationally intensive compared to a deep learning network, for example.

An image preview can be generated of an image that has an IQ closest to the image acquisition prescription (e.g., computed by the first network). A second network (e.g., a deep learning network, etc.) learns IQ metrics periodically from obtained site images and updates the first network to improve the first network's generation of corresponding image acquisition parameters.

The first network and second network can be provided together or separately in an image quality control framework. The first network and/or the second network can be deployed on a cloud, an edge device, an imaging device, etc., to streamline or "lighten" a host system and to aid in connecting MR scanners and/or other imaging devices in a healthcare facility (e.g., a hospital, a clinic, a surgical center, a doctor's office, etc.).

In certain examples, the image acquisition parameter configuration proceeds without iteration to reduce setup and image acquisition time. Instead, the first network is leveraged to generate settings for an image acquisition, while the second network operates separately and in parallel to gather and model information and periodically update and/or regenerate and redeploy the first network model. In addition, an expected image quality and scan time can be set before the scan is performed.

Certain examples select preferred, beneficial, or "optimal" parameters for prescription of a variety of acquisition applications for MR imaging and/or other imaging technologies. For example, a compromise or "trade-off" can be determined between image quality (e.g., signal-to-noise ratio (SNR) and contrast, etc.) and scan time based on the patient, study/scan type, reason for examination, etc. This trade-off or balance is very important in MR imaging, for example, at least in part because prescribing for good image quality (e.g., as represented by SNR and contrast, etc.) by keeping scan time low is a difficult or complicated task for MR imaging technologists.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters.

Learning refines the machine parameters, and, by extension, the connections between neurons in the network, such that the neural network behaves in a desired manner.

II. DESCRIPTION OF EXAMPLES

Example Imaging Systems and Methods

Figure 2:
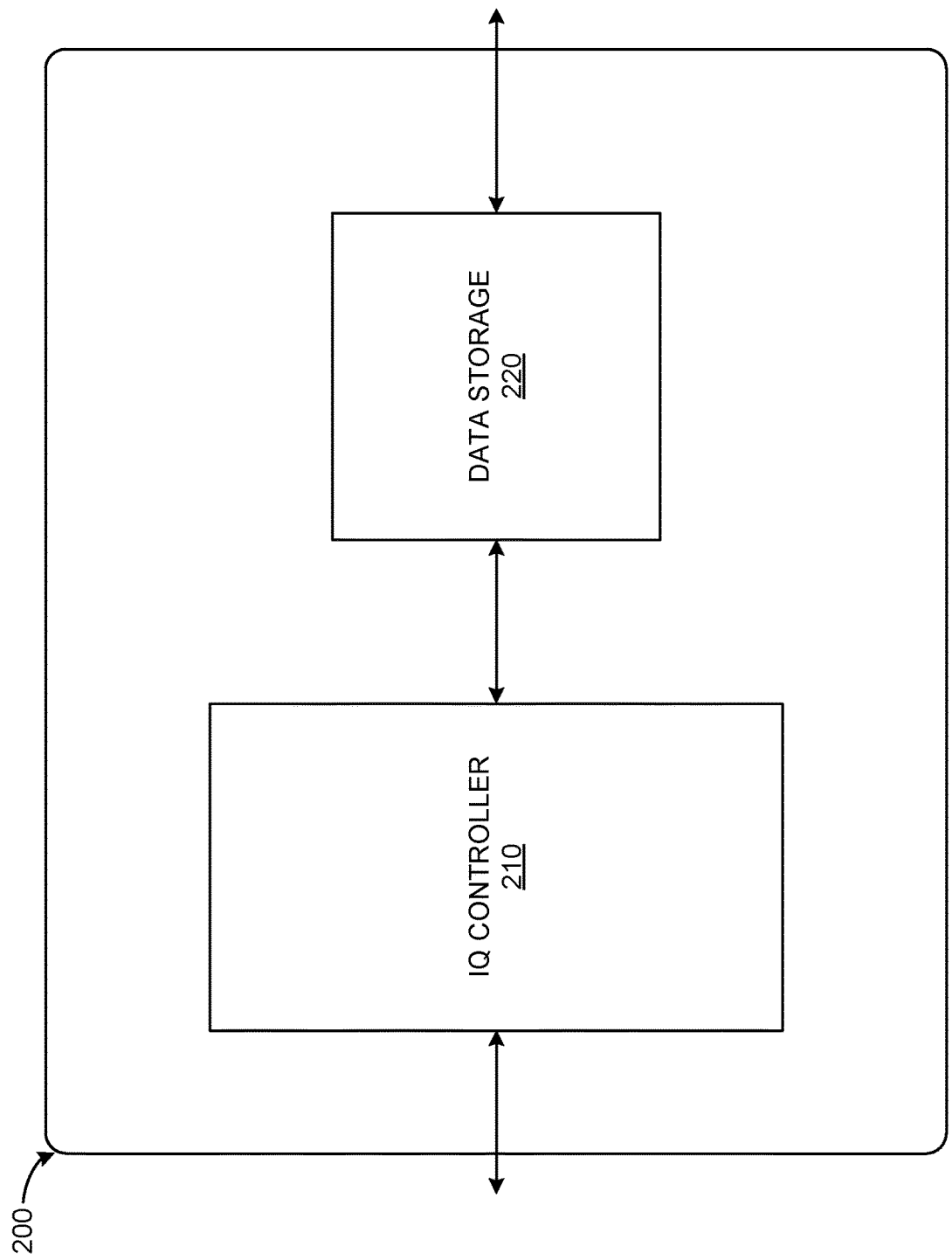

The methods, apparatus, and articles of manufacture described herein can be applied to a variety of healthcare systems. In one particular example, the methods, apparatus, and articles of manufacture described herein can be applied to the components, configuration, and operation of a magnetic resonance imaging system. FIGS. 1-2 illustrate an example implementation of a magnetic resonance imaging scanner apparatus to which the methods, apparatus, and articles of manufacture disclosed herein can be applied.

FIG. 1 shows major components of an example magnetic resonance imaging (MRI) system 10. Operation of the system is controlled from an operator console 12, which includes a keyboard and/or other input device 13, a control panel 14, and a display screen 16. The input device 13 can include a mouse, joystick, keyboard, track ball, touch activated screen, light wand, voice control, and/or other input device, and can be used for interactive geometry prescription, etc. The console 12 communicates through a link 18 with a computer system 20 that enables an operator to control the production and display of images on the display screen 16. The computer system 20 includes modules that communicate with each other through a backplane 20a. The modules of the computer system 20 include an image processor module 22, a central processing unit (CPU) module 24, and a memory module 26 that may include a frame buffer for storing image data arrays, for example. The computer system 20 is linked to archival media devices, permanent or back-up memory storage or a network for storage of image data and programs and communicates with a separate MRI system control 32 through a high-speed signal link 34. The computer system 20 and the MRI system control 32 collectively form an "MRI controller" 33.

The MRI system control 32 includes a set of modules connected together by a backplane 32a. These modules include a CPU module 36 as well as a pulse generator module 38. The CPU module 36 connects to the operator console 12 through a data link 40. The MRI system control 32 receives commands from the operator through the data link 40 to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to several components that are operated by the MRI controller 33, including the pulse generator module 38 (which controls a gradient amplifier 42, further discussed below), a physiological acquisition controller (PAC) 44, and a scan room interface circuit 46.

The CPU module 36 receives patient data from the physiological acquisition controller 44, which receives signals from a number of different sensors connected to the patient, such as ECG signals from electrodes attached to the patient. The CPU module 36 receives, via the scan room interface circuit 46, signals from various sensors associated with the condition of the patient and the magnet system. The scan room interface circuit 46 also enables the MRI controller 33 to command a patient positioning system 48 to move the patient or client C to a desired position for the scan.

The pulse generator module 38 operates the gradient amplifiers 42 to achieve desired timing and shape of the gradient pulses that are produced during the scan. The gradient waveforms produced by the pulse generator module 38 are applied to the gradient amplifier system 42 having Gx, Gy, and Gz amplifiers. Each gradient amplifier excites a corresponding physical gradient coil in a gradient coil assembly, generally designated 50, to produce the magnetic field gradients used for spatially encoding acquired signals. The gradient coil assembly 50 forms part of a magnet assembly 52, which also includes a polarizing magnet 54 (which, in operation, provides a homogeneous longitudinal magnetic field B0 throughout a target volume 55 that is enclosed by the magnet assembly 52) and a whole-body RF coil 56 (which, in operation, provides a transverse magnetic field B1 that is generally perpendicular to B0 throughout the target volume 55). In certain examples, the RF coil 56 is a multi-channel coil. A transceiver module 58 in the MRI system control 32 produces pulses that are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 32 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either transmit mode or receive mode.

After the multi-channel RF coil 56 picks up the RF signals produced from excitation of the target, the transceiver module 58 digitizes these signals. The MRI controller 33 then processes the digitized signals by Fourier transform to produce k-space data, which then is transferred to a memory module 66, or other computer readable media, via the MRI system control 32. "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media 66. This raw k-space data is rearranged into separate k-space data arrays for each image to be reconstructed, and each of these k-space data arrays is input to an array processor 68, which operates to Fourier transform the data into an array of image data. This image data is conveyed through the data link 34 to the computer system 20, where it is stored in memory. In response to commands received from the operator console 12, this image data may be archived in long-term storage or it may be further processed by the image processor 22 and conveyed to the operator console 12 and presented on the display 16.

In certain examples, the MRI controller 33 includes an example image quality (IQ) controller implemented using at least one of the CPU 24 and/or other processor of the computer system 20A and/or the CPU 36 and/or other processor of the system control 32A and/or a separate computing device in communication with the MRI controller 33. FIG. 2 shows an example implementation of an image quality control system including an IQ controller 210 and an associated data storage 220 (e.g., implemented in the memory 26 and/or the memory 66, etc.).

In certain examples, based on prescribed, desired IQ metrics and/or other settings, the IQ controller 210 provides an intelligent model (e.g., a deep learning network model, etc.) to generate scan parameters for a scan scenario.

Current MR image scanning involves usage of multiple applications/sequences based on a body part to be imaged and clinical aspects under study. These imaging applications and/or sequences are effectuated through selection of a large number of quantitative input scan parameters, such as a scan repeat time, scan resolution, inter-echo spacing, bandwidth, time-to-echo, etc. In all, about twenty to forty input parameters are typically available for operator manipulation. These parameters are not, however, fully independent, insofar as the setting of one parameter, such as the bandwidth, typically changes or limits the dynamic range of other parameters, such as the scan time.

The wide variety of type and value of input scan parameters often introduces practical limitations on obtained image quality. For example, clinical MR imaging systems are usually operated by technologists who often have limited knowledge of the physical interrelations between the various parameters. Clinical MR imaging systems are also usually operated under significant time constraints in which patient throughput is an important consideration. Imaging under these conditions is often performed using sub-optimal parameter values, and these sub-optimized imaging conditions lead to degraded image quality that can limit the clinical value of the results. It would be beneficial if the technician can only provide inputs about the scan such as pulse sequence, anatomy, etc., along with desired IQ performance indices (such as signal-to-noise ratio (SNR), contrast etc.) and leave the rest of the parameters to be filled optimally by a smart model for the system to scan.

In certain examples, the IQ controller 210 includes a "smart" model that is self-tuned to learn and is updated based at least in part on a usage pattern at a customer site and/or across systems in a customer network. In certain examples, the data storage 220 is also queried with scan parameters obtained from a network model, and preview of an image scanned with the same or similar scan parameters in the customer network can be displayed for confirmation of the scan parameters/settings. In certain examples, the image preview is a preview of an MR image scanned previously using the same network model and prescription settings closest to a model output. A user can modify those settings based on their own expertise, previous scans, etc.

While optimal parameter usage over a plurality of MR applications is impractical and unavailable, a neural network model can provide optimal or otherwise improved parameter settings and system usage. Additionally, dependency on user expertise and user attention to prescribe appropriate scan parameters is alleviated while improving image quality.

In certain examples, the smart model of the IQ controller 210 includes two neural or other machine learning networks: networks A and B. Network A provides an improved or optimal set of scan parameters for a given minimal set of inputs such as pulse sequence type, contrast type, desired SNR, contrast, anatomy, etc. At the end of a scan using these scan parameters, a generated image is installed in the data storage 220. Network B then calculates IQ metrics, such as SNR and contrast, etc., from the scanned images. Using these measured metrics along with scan parameters from the acquired image, network A is then fine-tuned, for example.

Additionally, scan parameters provided by network A can be used by the IQ controller 210 to query images stored in a database of the data storage 220 (e.g., a standalone image database, a cloud image database, another shared or group image database, etc.) to provide a preview image for which the same or similar scan parameters were previously used by the imaging system (e.g., MR system 10, etc.). Thus, a user can view generated scan parameters as well as a preview image associated with those scan parameters to determine whether to approve/confirm usage of those scan parameters, modify the scan parameters, request generation of new scan parameters from network A, etc.

Example Learning Network Systems

Figure 3:
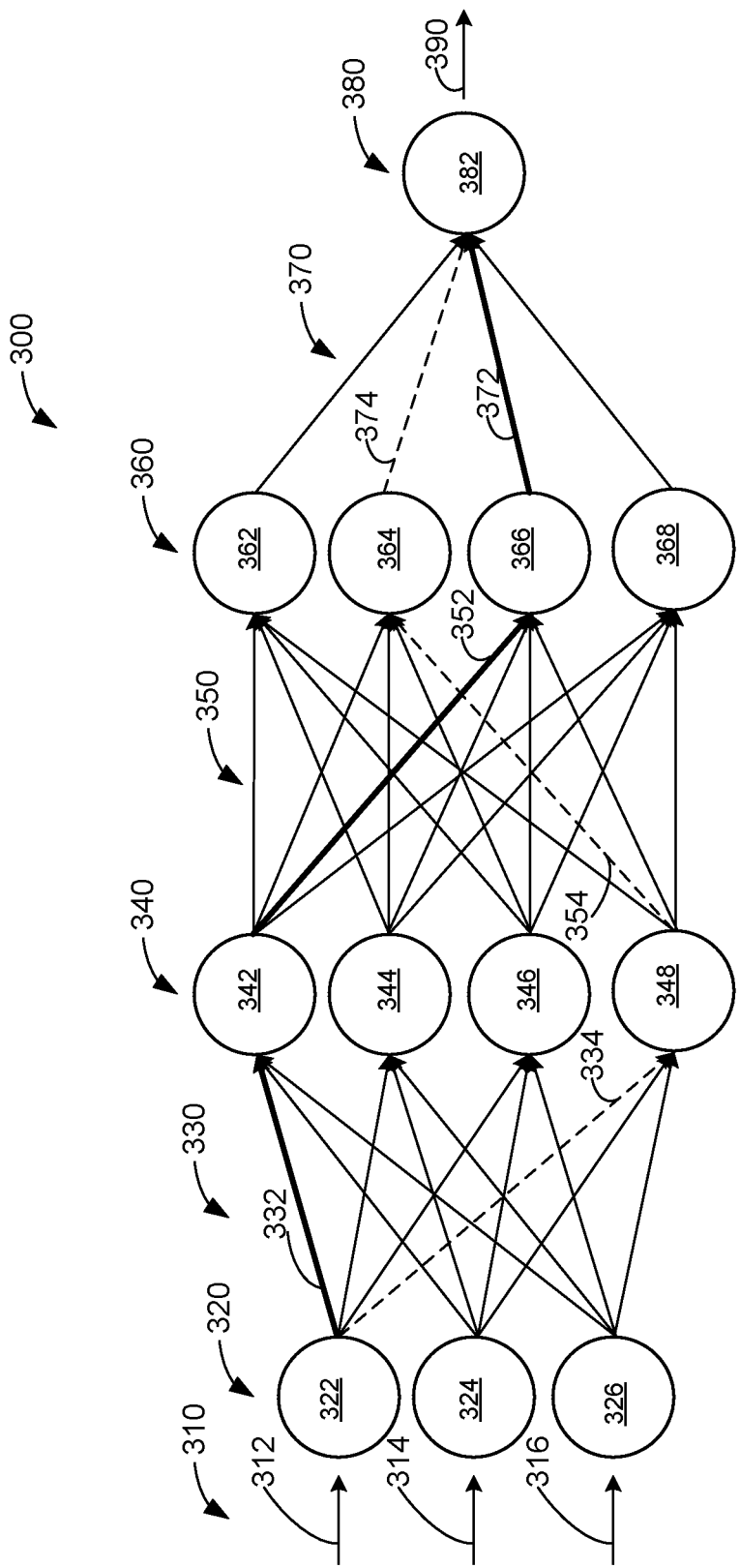
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Example Image Quality Systems and Methods

Figure 4:
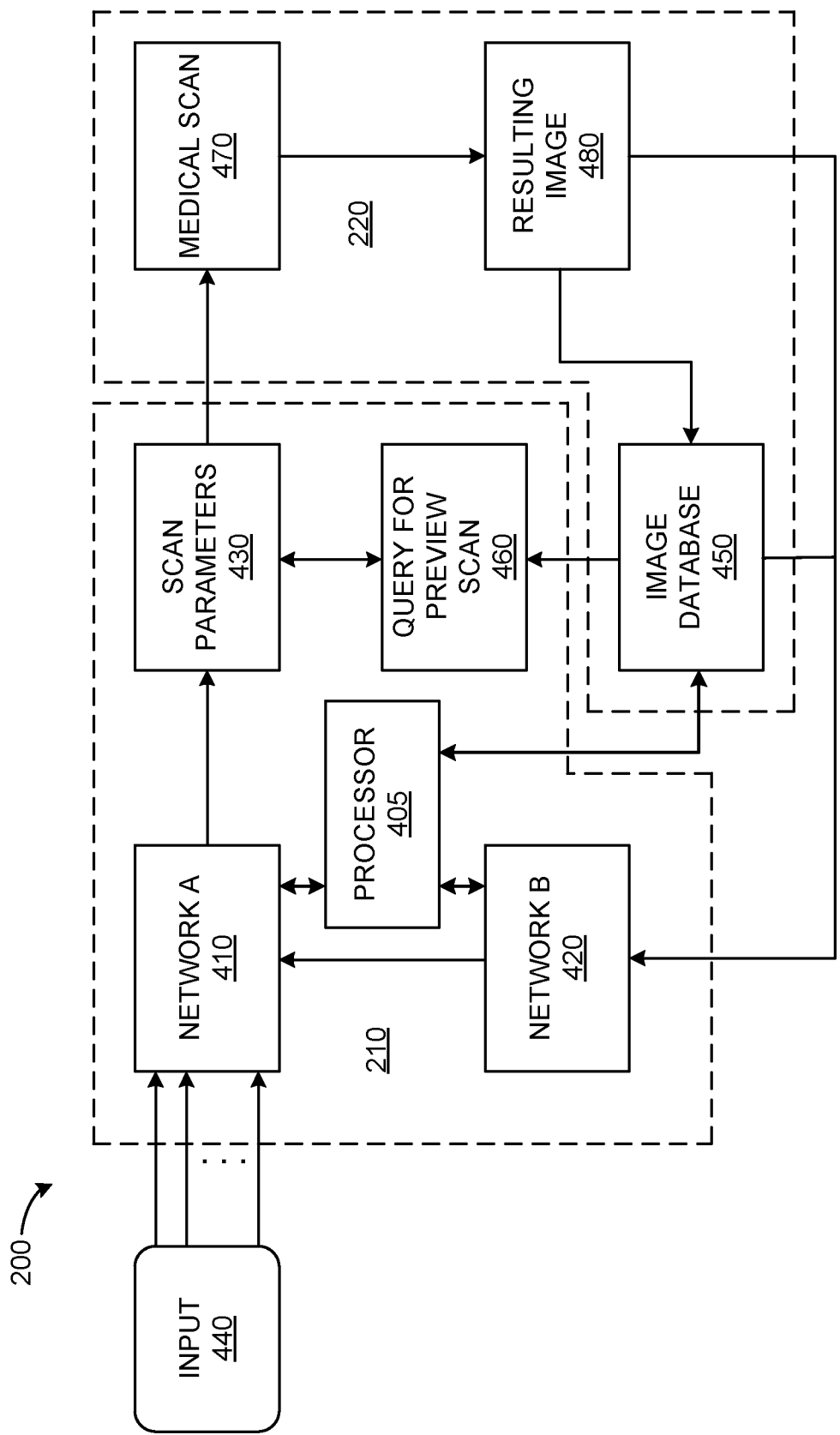
FIG. 4 illustrates an example implementation of the control system of FIG. 2.

FIG. 4 illustrates an example implementation of the IQ control system 200 of FIG. 2. In the example of FIG. 4, the IQ controller 210 includes a processor 405, a first neural network 410, and a second neural network 420. The example processor 405 is to generate a configuration for an imaging device/scanner/system for image acquisition. The processor 405, controller 210, and/or all of the control system 200 can be located in the imaging device, in a workstation attached to and/or otherwise in communication with the imaging device, in a cloud-based server, in an edge device, and/or in another computing device, etc.

In certain examples, the first neural network 410 is a trained shallow neural network with fewer layers and nodes (e.g., weighted inputs provided to a layer of radial basis functions to provide linear weights to an output, etc.), such as a regression neural network, etc. In certain examples, the second neural network 420 is a more complex neural network such as a trained deep neural network (e.g., a deep convolutional neural network, other deep learning network, etc.) with a plurality of nodes and many hidden layers, etc.

For example, the shallow neural network has one hidden layer, while the deep neural network has a plurality of hidden layers. That is, the shallow network has an input layer, a hidden layer, and an output layer, and the deep network has an input layer, multiple hidden layers, and an output layer. In certain examples, to try and fit the same function, the shallow network involves a greater number of parameters than the deep network. Through multiple layers, the deep network is able to fit functions with fewer parameters than the shallow network, for example.

As shown in the example of FIG. 4, the first neural network 410 generates optimal or improved scan parameters 430 based on input 440 such as anatomy (e.g., head, cardiac, chest, lung, leg, arm, etc.), pulse sequence diagram (PSD) type (e.g., spin echo (SE), gradient echo (GE), diffusion-weighted imaging (DWI), echo-planar imaging (EPI), etc.), image type (e.g., T1-weighted images with fat tissue bright, T2-weighted images with fat tissue and water bright, proton density (PD)-weighted images, etc.), field of view (FOV), signal-to-noise ratio (SNR), contrast, patient comfort, scan time efficiency, etc.). The scan parameters 430 can be used by the processor 405 to query an image database 450 for a preview image 460. The preview image 460 can be reviewed by a user and/or processed automatically by an image processing program to verify that the scan parameters 430 will or are likely to produce an image suitable for study/review/examination purposes. If the preview image 460 is unsuitable or otherwise unsatisfactory/unacceptable, then the scan parameters 430 can be adjusted (e.g., manually, automatically by software, by requesting new parameters 430 from the network 410, etc.).

In certain examples, a complete set of scan parameters 430 for image acquisition can be generated by the network 410. In other examples, a partial set of scan parameters 430 for image acquisition is generated by the network 410, and the user and/or other application provides the remaining parameters for an image acquisition prescription. For example, a technician can provide high-level information for a protocol to be scanned, such as coil, anatomy, pulse sequence, and field of view. The remaining parameters are auto-filled in the imaging prescription based on required and/or desired IQ metrics driving parameter output from the network 410. For example, slice thickness (ST), flip angle (FA), echo time (TE), repetition time (TR), inversion time (TI), echo train length (ETL), spatial resolution (e.g., Xres in an x direction, Yres in a y direction, Zres in a z direction, etc.), number of excitations (Nex), number of signal averages/acquisitions (Nsa), receiver bandwidth (rBW), etc., can be generated using the neural network 410.

Once the scan parameters 430 are confirmed, the parameters 430 are used by the imaging system to perform a medical image scan 470 to generate a resulting image 480 (e.g., provided to the imaging system using the processor 405, etc.). The resulting image 480 can be displayed to a user, fed into another application for image clean-up, computer-aided detection, image quality analysis, feedback for improvement of the network 410, stored in the image database 450, and/or otherwise processed, for example. The image 480 can be used as a subsequent preview image 460 as well as in conjunction with one or both neural networks 410, 420, for example.

Thus, expected outcomes (e.g., expected image quality, etc.) can be fed as an imaging prescription (e.g., including FOV, SNR, contrast, scan time, patient comfort level, etc.) into the neural network 410 (e.g., located on a cloud and/or edge device and/or imaging device, etc.). The network 410 provides output (e.g., ST, slice, FA, TE, TR, TI, ETL, Xres, Yres, Nex, rBW, etc.) to form and/or supplement scan parameters in the imaging prescription. In certain examples, the network 410 can self-tune based on a preview scan 460 from the database 450 and/or other expert scan processing. The deep learning network 420 receives the image 480 and leverages the image 480 (and image(s) from the database 450) to obtain IQ metrics (e.g., SNR, peak SNR, contrast, mean square error, peak mean square error, mean absolute error, structural similarity index, maximum difference, absolute difference, normalized cross-correlation, structural content, image fidelity, etc.) from the image data. The IQ metrics determined by the network 420 can be used to periodically (e.g., after an elapsed time, after a number of executions, after feedback registers more than a threshold number of errors in actual image quality versus desired/expected/requested image quality, etc.) update the network 410 and/or generate a new model to be deployed as the network 410, for example.

FIG. 5 illustrates an example on-the-fly network training environment 500 to generate parameters to train the shallow network 410. In some examples, the parameters 540 include IQ metrics 520 computed by the deep learning network 420 (e.g., with an input of a DICOM image, etc.), DICOM parameters 530 (e.g., TR, TE, matrix size, etc.), and other parameters 535 such as coil, anatomy, application, FOV, etc., for the network 410 to generate subsequent image acquisition system parameters 430. As shown in the example of FIG. 5, the captured image 1080 and/or other scanned image(s) 510 (e.g., from the database 450, from cloud and/or site scans, etc.) are processed to compute IQ metrics 520 such as SNR, contrast, scantime efficiency, etc. IQ metrics 520 can be provided with pulse sequence parameters 530, such as TR, TE, matrix size, etc., and other scan parameters 535 such as coil, anatomy, application, FOV, etc., which can be extracted from the image dataset, to generate parameters 540 (e.g., network weights, modifiers, values, etc.) for the network 410 to generate subsequent image acquisition system parameters 430.

Using the example process of FIG. 5, the trained neural network model 410 can be updated and/or redeployed based on the parameters 540 from the training environment 500. Furthermore, the updated/redeployed network 410 can be tested and validated before being released for operation. For example, images 510 gathered at a particular site can be used by the network 420 to generate training parameters 540 to train the network 410 to generate improved or "optimal" scan parameter 430 at that particular site. In certain examples, cloud-based and/or other centralized storage 450 can enable site-based and/or region-/network-based analysis of images 510 and to train/update the shallow network 410 for a particular site, a group of sites, etc., by using the parameters 540 generated by the network training environment 500.

FIG. 6 illustrates an example testing and validation phase 600 to confirm that the updated network 410 is ready to be deployed to configure imaging systems for image acquisition. As shown in the example of FIG. 6, input 610 including high-level parameters 535 such as coil, anatomy, application, FOV, etc., can be provided along with minimum, desired, and/or required IQ metric values 615 (e.g., required minimum or threshold values for SNR, contrast, scantime efficiency, etc.) to the trained network 410. The trained network 410 produces scan parameters 430 which are used to perform a medical image scan 470. IQ metrics 620 may be calculated for the image 480 resulting from the scan 470 and can then be compared to the specified IQ metrics 615 to verify that the specified IQ metric values 615 are met in the resulting image 480, for example.

If the computed IQ metrics 620 match the target IQ metrics 615, then the network 410 is ready to be (re)deployed. For example, the computed metrics 620 may be identical or very close to the target metrics 615. In certain examples, the computed metrics 620 may be within a threshold, standard deviation, margin of error, etc., and be considered to "match" the target metrics 615. For example, if the computed metrics 520 are within 5% of the target metrics 615, are within +/−0.01 of the target metrics 615, etc., then the computed metrics 620 can be considered to "match" the target metrics 615 for purposes of the network model 410. The tolerance or margin of error may vary, however, based on the particular metric, reason for exam, patient, application, imaging scanner, etc. feedback 630 can be provided to the network 410 to adjust network weight(s), apply a modifier, reconfigure network connections, etc. Testing 600 can then be redone to determine whether the updated computed metrics 620 now match the target metrics 615 within an acceptable/specified tolerance, for example.

Thus, in certain examples, network model(s) 410 and/or 420 are built using training data including IQ metrics, such as SNR, contrast, etc., computed using scanned images in imaging scanners available across image review stations and from a plurality of databases. Networks 410, 420 are then trained using these data to meet a target output. Once the training is completed, the efficacy of the network 410, 420 is then tested with a different set of known input and output data. Training continues until the network output matches or is close to the known output during the testing phase. The network architecture helps to maintain high network efficacy to follow the variations in the input data.

Once the networks 410 and 420 are deployed to a site, the network model 410 is periodically fine-tuned to follow a usage pattern associated with/observed at the site based on the output of the network 420 that calculates IQ metrics from image scans. Thus, the network model 420 helps to ensure that particularities of the image scanner/site are taken into account when generating input to the network model 410, which will then generate scan parameters 430 tailored to the particular site, scanner, group, etc.

Current MR scanning involves usage of multiple applications/sequences, and each sequence requires tuning of multiple parameters to obtain reasonably good images. A technician needs to have knowledge of tuning the parameters, which involves time-consuming manual work for each patient and each workflow. For a less-trained technician, it would be a challenging task to produce optimal images with a variety of scenarios. Thus, certain examples provide technological improvement to prior limited imaging control systems to include first and second neural network models 410, 420 to automatically generate and configure parameters 430 to configure the imaging scanner for image acquisition. As a result, the configuration program, technician, etc., only selects high level parameters such as required pulse sequence (task), anatomy, coil, scan region of interest (ROI), and IQ and performance metrics (such as SNR, contrast, etc.), and remaining parameters are filled optimally by an intelligent system.

Using this system, MR imaging is simplified for technician view and produces optimal and/or otherwise improved IQ metrics. This system provides technological improvement to the MR and/or other imaging ecosystem and generates new models, new settings, etc., to extend the technological capabilities of the imaging scanner and improve image quality. The system dynamically learns better imaging prescriptions based on fewer parameters as well as a system usage pattern at site or customer group of sites. The system leverages protocols scanned across the hospital network to auto suggest best possible image quality that can be obtained on the system.

Certain examples provide an "intelligent" scanner that is always learning new ways to acquire images (and acquire better images) such as to simplify the complex MR modality. Automated workflow and new models enable benefits to be shared across imaging scanners to provide collaboration and improve care to customers, while giving an advantage to the business. Certain examples help insure uniform use of the system and provide a framework to incorporate the best use of an application and provide feedback for low IQ performance back to engineering.

Figure 7:
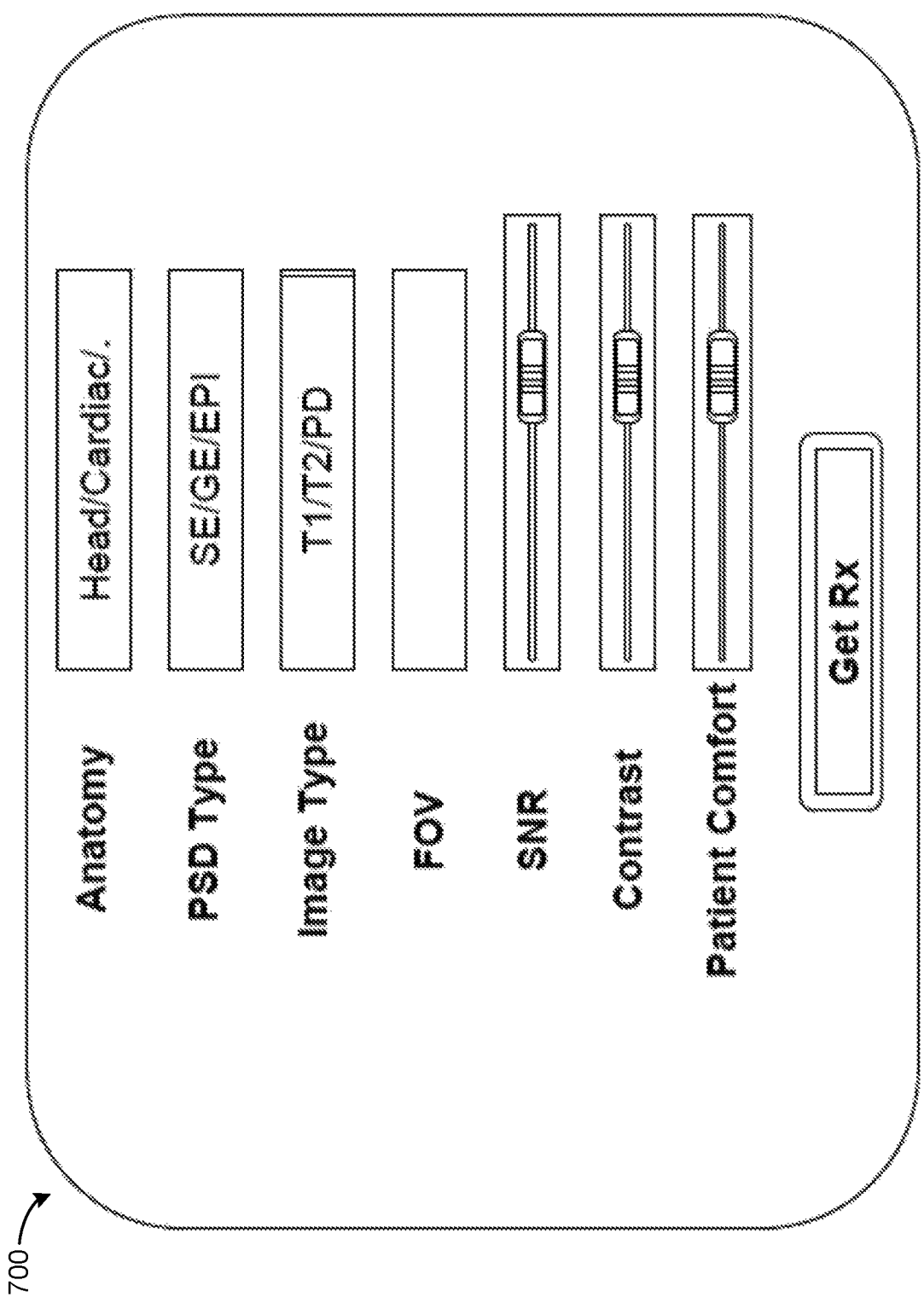
FIGS. 7-9 show example interfaces displayed and/or otherwise made available for interaction for input of parameter, metric, and/or other information to be used by the network(s), imaging system, etc.
Figure 8:
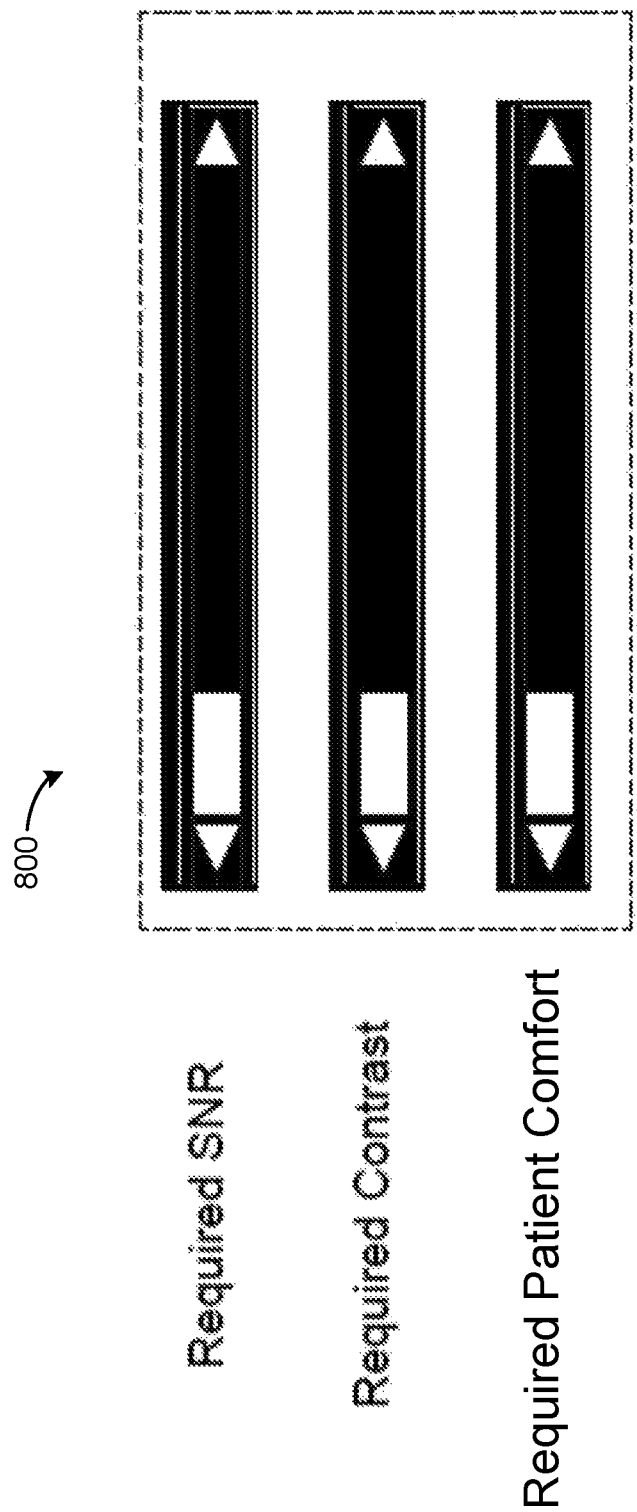
Figure 9:
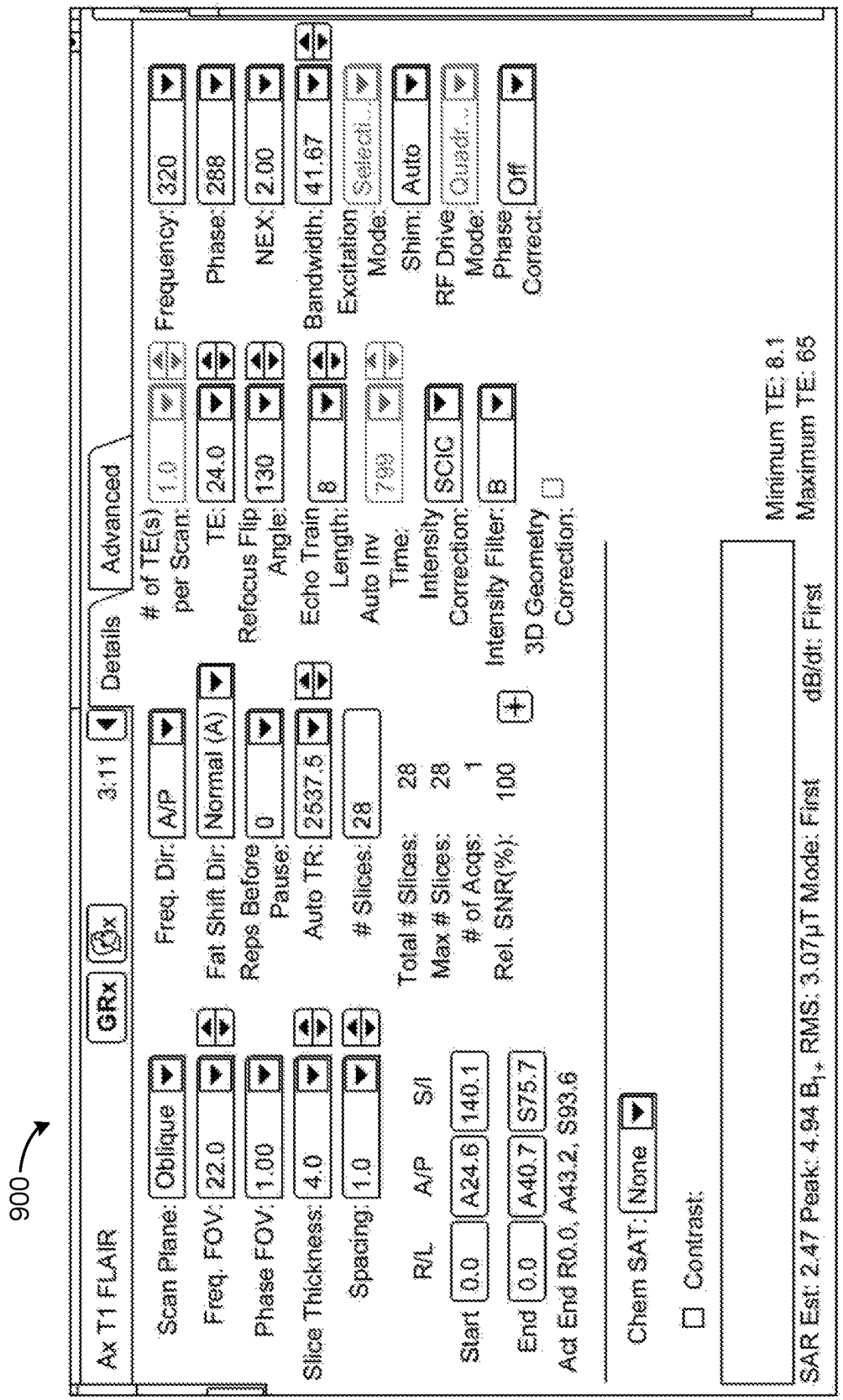

FIGS. 7-9 show example interfaces 700-900 displayed and/or otherwise made available for interaction for input of parameter, metric, and/or other information to be used by the processor 405, network(s) 410, 420, imaging system, etc. As shown in the example of FIG. 7, an example input interface 700 allows a user to specify an anatomy, a PSD type, an image type, a FOV, a target SNR, a target contrast, a target patient comfort level, etc., as input 440 to submit to the shallow neural network 410 to generate scan parameters 430 for image acquisition.

FIG. 8 shows example sliders 800 to allow a user to specify a required SNR, contrast, and scantime efficiency (e.g., correlated to patient comfort level) for the input 440. For example, a user can set the SNR, contrast, and patient comfort level to be "low," "medium," or "high" by moving respective sliders in the interface. In some examples, more options than "low," "medium," and "high" are available. For example, a scale of one to five (1-5), one to ten (1-10), or the like, can be provided for the user to select by moving the respective sliders.

FIG. 9 depicts an example interface 900 including example scan parameters 430 to configure an imaging system for image acquisition. The example interface 900 can be populated with scan parameters 430 generated by the network 410, for example.

In certain examples, the shallow network model 410 and/or the deep learning network model 410 can be deployed as a model-as-a-service, running locally, on a cloud-based server, and/or via an edge device, etc. In certain examples, the model 410 and/or the model 420 can run on the MR scanner itself, on a workstation connected to the scanner, etc. In certain examples, a cloud- and/or edge-based model 410 and/or 420 can configure and distribute scan parameters 430 to a plurality of imaging scanners.

In certain examples, the model 410 and/or the model 420 can be periodically regenerated (e.g., by running a script at an interval such as two weeks, etc., to gather information to generate, train, test, and deploy the model 410 and/or the model 420, etc.). In certain examples, information can be retrieved from the imaging scanner itself, instead of and/or in addition to the database 450. In certain examples, multiple models 410 and/or 420 can be generated for 2D and/or 3D imaging. In other examples, the same model 410 and/or 420 is used for both 2D and 3D imaging.

In certain examples, the model 410 and/or 420 is trained for a particular imaging system type. In certain examples, a variation is system behavior can be modeled, and a deviation in actual system behavior from expected system behavior can be determined and modeled, for example. An updated configuration for a deviating system can be generated by the model 410 and provided to the imaging scanner, for example. Alternatively or in addition, an alert can be triggered for another system and/or operator, maintenance can be scheduled, etc.

Certain examples provide a cloud-based solution that is constant and self-learning to enable a simplified, automated workflow with an intelligent scanner. Certain examples provide increased throughput due to a reduction in image acquisition prescription time. Certain examples provide increased productivity with consistent and reliable quality. In certain examples, rather than computationally expensive optimization algorithms, the network model 410 is developed based on a real image data set and is tuned based on a usage pattern for a device, a site, a group, etc.

While example implementations are illustrated in conjunction with FIGS. 1-9 elements, processes and/or devices illustrated in conjunction with FIGS. 1-9 can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 10:
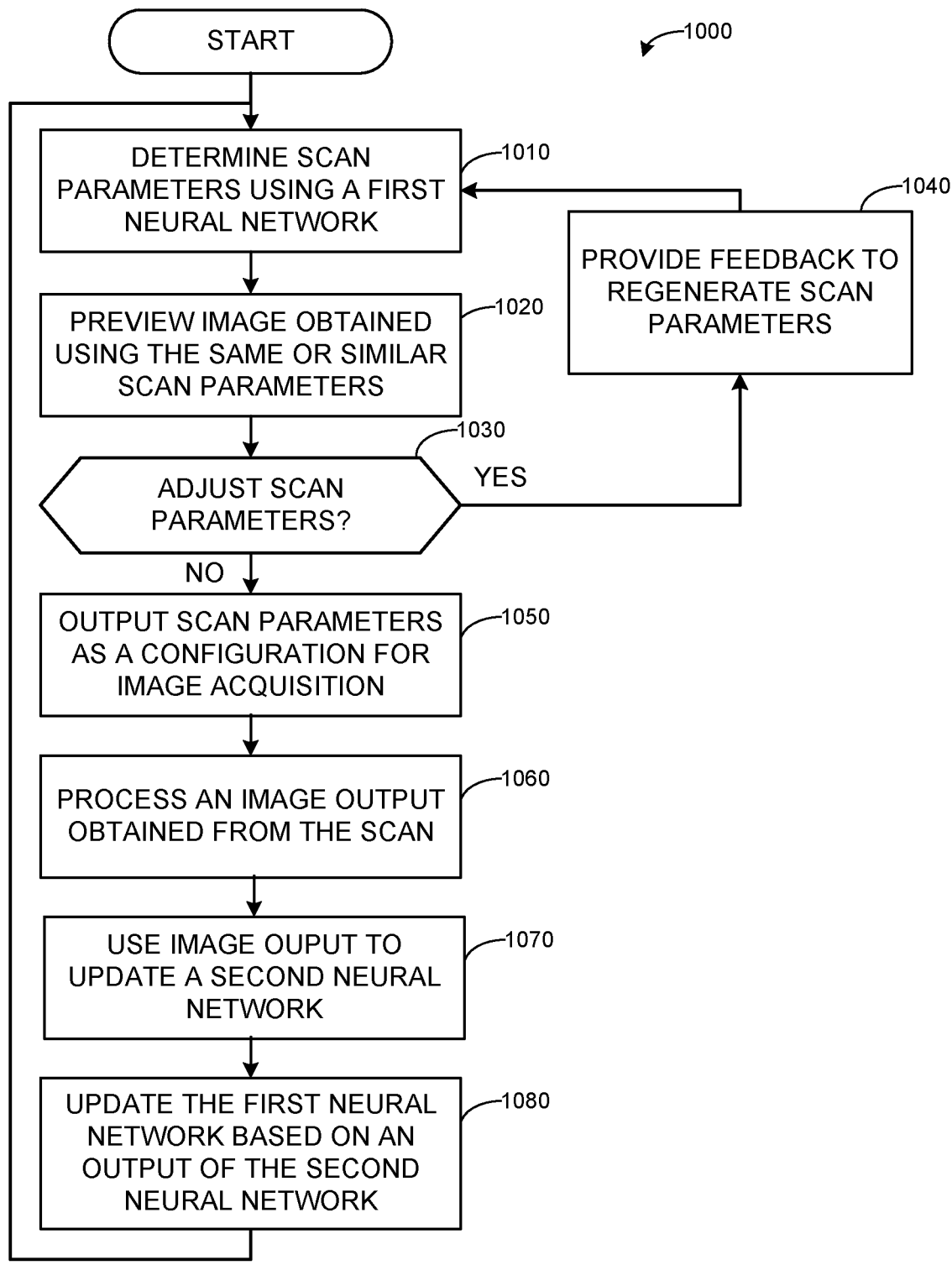
FIG. 10 illustrates a flow diagram of an example method for machine learning-driven configuration of an imaging system for image acquisition.

Flowcharts representative of example machine readable instructions for implementing components disclosed and described herein are shown in conjunction with at least FIG. 10. In the examples, the machine readable instructions include a program for execution by a processor such as the processor 1112 shown in the example processor platform 1700 discussed below in connection with FIG. 11. The program may be embodied in machine readable instructions stored on a tangible computer readable storage medium such as a CD-ROM, a floppy disk, a hard drive, a digital versatile disk (DVD), a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowcharts illustrated in conjunction with at least FIG. 10, many other methods of implementing the components disclosed and described herein may alternatively be used. For example, the order of execution of the blocks may be changed, and/or some of the blocks described may be changed, eliminated, or combined. Although the flowcharts of at least FIG. 10 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIG. 10 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIG. 10 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 1000 depicted in FIG. 10, an imaging system (e.g., an MRI scanner, etc.) can be automatically configured by a combination of two learning network models that dynamically adjust to the particular imaging system and scan type to generate optimal, beneficial, and/or otherwise improved scan parameters to set the imaging system for the scan.

At block 1010, scan parameters 430 can be determined using a first neural network. For example, target IQ metrics and other scan parameters are input to the shallow network 410, which produces a set of scan parameters 430 to configure an imaging scanner for image acquisition (e.g., for an abdominal scan using a GE MRI scanner, for a cardiac scan using an ACME MRI scanner, etc.).

At block 1020, an image 460 obtained using the same or similar scan parameters 430 is previewed. For example, an image 460 stored in the database 450 can be retrieved based on the processor 405 matching the set of scan parameters 430 generated by the shallow network 410 to stored images in the database 450 that are stored in association with the scan parameters used to obtain them. Thus, the image 460 can be located in the database 450 by querying for the scan parameters to match (e.g., exactly or within a tolerance/range/threshold/margin of error, etc.) the generated scan parameters 430.

At block 1030, the preview image 460 is evaluated to determine whether the associated scan parameters 430 will produce an image that is usable for its intended purpose or whether the scan parameters 430 should be adjusted to produce a different image. For example, the preview image 460 may not be of sufficient quality to enable diagnosis by a radiologist. The preview image 460 may be of too high quality for the intended review, thereby taking an unnecessary amount of time, for example. A computer program executed using the processor 405 and/or a user can evaluate the preview image 460 to determine whether the scan parameters 430 are to be adjusted. If so, at block 1040, feedback is provided to regenerate the scan parameters 430 via the first network (e.g., the shallow network 410) at block 1010.

At block 1050, the scan parameters 430 are output as a configuration for image acquisition 470. For example, the imaging scanner is sent a file, profile, and/or other set of configuration settings via the processor 405 using the scan parameters 430 to automatically configure the scanner for image acquisition.

At block 1060, an image output 480 obtained from the scan 470 is processed. For example, the resulting image 480 can be added to the database 450, the image 480 can be pre-and/or post-processed to clean up the image 480, etc. At block 1070, the image output 480 is used by the processor 405 to update a second neural network. For example, the image output 480 is provided to the deep learning network 420, which extracts image quality metrics and/or other information from the image 480. Using the IQ metrics and/or other information extracted from the image 480 and/or other database 450 information, the network 420 can generate updated settings (e.g., network weights, etc.) for the shallow network 410.

At block 1080, the first network is updated based on an output of the second network. For example, the deep learning network 420 provides weights, configuration, etc., to the shallow network 410 based on the processing of the resulting image 480 by the deep network 410. Then, on a subsequent image acquisition, the first network has an updated configuration to use in generating scan parameters 430 for that scan 470.

Thus, certain examples provide a dual-network model system including a trained shallow neural network model 420 and a trained deep neural network model 410 to automatically configure an imaging system for image acquisition according to one or more target image quality metrics. Using target IQ metrics and the neural networks, certain examples provide outcome-based parameter input to drive imaging system configuration and diagnostic quality image acquisition.

In certain examples, a first network (e.g., a shallow network) provides the scan parameters (e.g., IQ criteria, etc.), and a second network (e.g., a deep network) tunes the first network and keeps the first network model updated based on a usage pattern. Scanned images can be used for training and to extract IQ metrics from the images, which can be used to update the model. Thus, the shallow network model is created, and the deep network model updates/redeploys the shallow network model by tuning the shallow network model to the particular usage pattern of the site. The deep learning network model processes images that are obtained and generates parameters to update the shallow learning network model so that, for example, an abdominal scan causes the deep network 420, via the processor 405, to customize the shallow network 410 for the abdominal scan at the particular MR scanner, a cardiac scan triggers the deep network 420 to customize the shallow network 410 for the cardiac scan at the particular MR scanner, etc. Using an outcome-based description (e.g., SNR, FOV, etc.), the trained network takes scan parameters and computes values for a configuration set for an imaging scanner.

While some examples have been shown and described with respect to MR images, the same systems and methods can be applied to ultrasound, x-ray, MICT, CT, etc. In some examples, modalities can be combined such as applying a CT model to MR images, etc.

Figure 11:
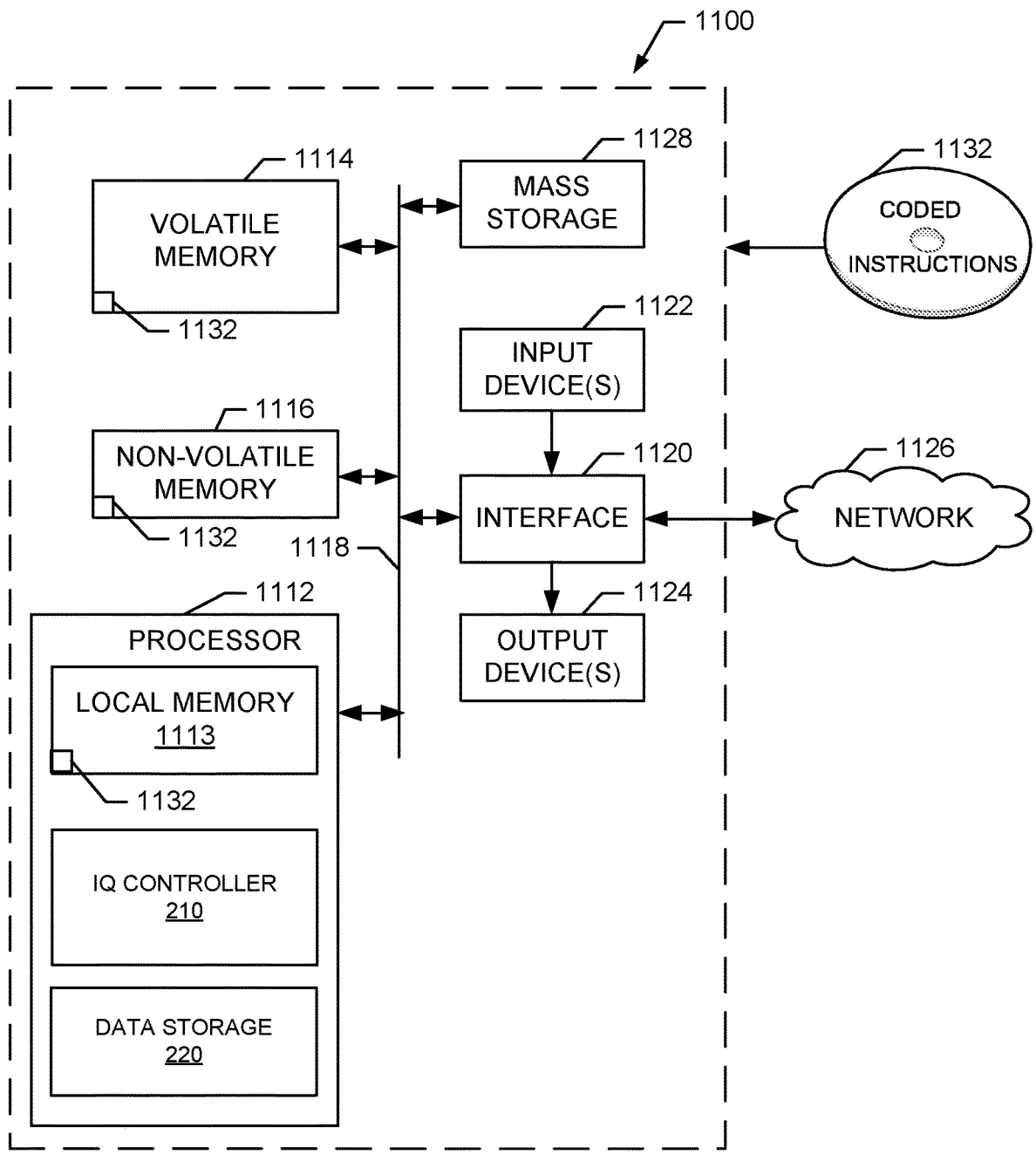
FIG. 11 is a block diagram of a processor platform structured to execute the example machine readable instructions to implement components disclosed and described herein.

FIG. 11 is a block diagram of an example processor platform 1100 structured to executing the instructions of at least FIG. 10 to implement the example components disclosed and described herein. The processor platform 1100 can be, for example, a server, a personal computer, a mobile device (e.g., a cell phone, a smart phone, a tablet such as an iPad™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by integrated circuits, logic circuits, microprocessors or controllers from any desired family or manufacturer.

The processor 1112 of the illustrated example includes a local memory 1113 (e.g., a cache). The example processor 1112 of FIG. 11 executes the instructions of at least FIG. 10 to implement the systems and infrastructure and associated methods of FIGS. 1-9 such as the example IQ controller 210 (and its processor 405 and networks 410, 412, etc.) and the example data storage 220 (including its database 450, etc.), etc. The processor 1112 of the illustrated example is in communication with a main memory including a volatile memory 1114 and a non-volatile memory 1116 via a bus 1118. The volatile memory 1114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 may be implemented by flash memory and/or any other desired type of memory device. Access to the main memory 1114, 1116 is controlled by a clock controller.

The processor platform 1100 of the illustrated example also includes an interface circuit 1120. The interface circuit 1120 may be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and commands into the processor 1112. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1120 of the illustrated example, thus, typically includes a graphics driver card, a graphics driver chip or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 of FIG. 11 may be stored in the mass storage device 1128, in the volatile memory 1114, in the non-volatile memory 1116, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:
1. An apparatus comprising:
 a memory storing a first neural network that is trained to map image quality metrics to corresponding scan parameters; and a processor configured to:
- receive specified image quality metrics;
- instruct the trained first neural network to generate scan parameters based on the specified image quality metrics to configure an imaging device for image acquisition;
- query a database to retrieve a preview image based on the scan parameters generated by the trained first neural network;
- trigger, based on an analysis of the preview image, the trained first neural network to regenerate the scan parameters when the analysis of the preview image does not satisfy an image quality criterion; and
- instruct the imaging device to acquire one or more resulting images using the scan parameters.

2. The apparatus of claim 1, further including a second neural network that is trained to map image datasets to corresponding image quality metrics, wherein the first neural network is trained by the image quality metrics output from the second neural network and scan parameters associated with corresponding image datasets.

3. The apparatus of claim 2, wherein the first neural network is a shallow neural network and the second neural network is a deep neural network, the second neural network including more hidden layers than the first neural network.

4. The apparatus of claim 2, wherein the second neural network is to periodically update the first neural network.

5. The apparatus of claim 1, wherein the first neural network is to be fine-tuned based on a usage pattern associated with at least one of the imaging device or a site at which the imaging device is located.

6. The apparatus of claim 1, wherein the imaging device is a magnetic resonance imaging device, the image quality metrics include at least one of signal-to-noise ratio (SNR), contrast, scan time, and patient comfort level, and the scan parameters include at least one of slice thickness (ST), flip angle (FA), echo time (TE), repetition time (TR), inversion time (TI), echo train length (ETL), spatial resolution, number of excitations (Nex), number of signal averages/acquisitions (Nsa), receiver bandwidth (rBW).

7. A non-transitory computer-readable storage medium storing:
- a first neural network that is trained to map image quality metrics to corresponding scan parameters; and
- instructions which, when executed, cause at least one processor to at least:
  - receive specified image quality metrics;
  - instruct the trained first neural network to generate scan parameters based on the specified image quality metrics to configure an imaging device for image acquisition;
  - query a database to retrieve a preview image based on the scan parameters generated by the trained first neural network;
  - trigger, based on an analysis of the preview image, the trained first neural network to regenerate the scan parameters when the analysis of the preview image does not satisfy an image quality criterion; and
  - instruct the imaging device to acquire one or more resulting images using the scan parameters.

8. The non-transitory computer-readable storage medium of claim 7, further storing a second neural network that is trained to map image datasets to corresponding image quality metrics, wherein the first neural network is trained by the image quality metrics output from the second neural network and scan parameters associated with corresponding image datasets.

9. The non-transitory computer-readable storage medium of claim 8, wherein the first neural network is a shallow neural network and the second neural network is a deep neural network, the second neural network including more hidden layers than the first neural network.

10. The non-transitory computer-readable storage medium of claim 9, wherein the instructions, when executed, cause the at least one processor to periodically update the first neural network using the second neural network.

11. The non-transitory computer-readable storage medium of claim 7, wherein the instructions, when executed, cause the at least one processor to fine-tune the first neural network based on a usage pattern associated with at least one of the imaging device or a site at which the imaging device is located.

12. A computer-implemented method comprising:
- training a first neural network, using image quality metrics and scan parameters associated with image datasets, wherein the image quality metrics are output from a second neural network that maps the image datasets to corresponding image quality metrics;
- receiving, by at least one processor, specified image quality metrics;
- generating, by the trained first neural network, corresponding scan parameters based on the specified image quality metrics to configure an imaging device for image acquisition;
- querying a database to retrieve a preview image based on the scan parameters generated by the trained first neural network;
- triggering, based on an analysis of the preview image, the trained first neural network to regenerate the scan parameters when the analysis of the preview image does not satisfy an image quality criterion; and
- instructing, by the at least one processor, the imaging device to acquire one or more resulting images using the scan parameters.

13. The method of claim 12, wherein the first neural network is a shallow neural network and the second neural network is a deep neural network, the second neural network including more hidden layers than the first neural network.

14. The method of claim 12, further including fine-tuning the first neural network based on a usage pattern associated with at least one of the imaging device or a site at which the imaging device is located.

15. The method of claim 12, further including:
- computing image quality metrics from the one or more resulting images using the second neural network; and
- updating the first neural network using the computed image quality metrics.

16. The method of claim 12, further including periodically updating the first neural network based on an analysis, by the second neural network, of images acquired by the imaging device using the scan parameters generated by the first neural network.

17. The method of claim 12, wherein the imaging device is a magnetic resonance imaging device, the image quality metrics include at least one of signal-to-noise ratio (SNR), contrast, scan time, and patient comfort level, and the scan parameters include at least one of slice thickness (ST), flip angle (FA), echo time (TE), repetition time (TR), inversion time (TI), echo train length (ETL), spatial resolution, number of excitations (Nex), number of signal averages/acquisitions (Nsa), receiver bandwidth (rBW).

* * * * *